US006616954B1

(12) United States Patent
Dally et al.

(10) Patent No.: US 6,616,954 B1
(45) Date of Patent: Sep. 9, 2003

(54) SOLVENT RELEASED ENCAPSULATED YEAST

(75) Inventors: Vernetta L. Dally, White Plains, NY (US); David E. Martin, Branchville, NJ (US); Carl J. Pacifico, West Milford, NJ (US); Paul H. Richardson, McAfee, NJ (US)

(73) Assignee: Balchem Corporation, Slate Hill, NY (US)

( * ) Notice: Subject to any disclaimer, the term of this patent is extended or adjusted under 35 U.S.C. 154(b) by 0 days.

(21) Appl. No.: 10/099,289

(22) Filed: Mar. 14, 2002

(51) Int. Cl.$^7$ ............... C12N 11/04; A23P 1/04; A21D 2/14
(52) U.S. Cl. ............... 426/19; 435/182; 426/62; 426/551; 426/561; 426/653
(58) Field of Search ............... 435/255.2, 255.21, 435/182; 424/93.51; 426/19, 62, 549, 551, 555, 561, 653

(56) References Cited

U.S. PATENT DOCUMENTS

| 4,719,114 | A | | 1/1988 | Percel |
|---|---|---|---|---|
| 5,275,943 | A | * | 1/1994 | DiTuro ............... 435/179 |
| 6,258,870 | B1 | * | 7/2001 | Hubbell et al. ............... 522/26 |

FOREIGN PATENT DOCUMENTS

| WO | WO95/34292 | 12/1995 |
|---|---|---|

* cited by examiner

*Primary Examiner*—Keith Hendricks
(74) *Attorney, Agent, or Firm*—Hoffmann & Baron, LLP

(57) ABSTRACT

The present invention is an encapsulated yeast composite comprising a core comprising yeast and a soluble coating comprising polyethylene glycol having a molecular weight less than 3050. The yeast includes *Saccharomyces cerevisiae*. The encapsulated composites are useful in the production of food compositions and food products.

46 Claims, No Drawings

SOLVENT RELEASED ENCAPSULATED YEAST

BACKGROUND OF THE INVENTION

The present invention relates generally to the art of food preparation, and, in particular, to the use of yeast in food.

Yeast is a living organism which is sensitive to its surrounding environment. Exposure of yeast to, for example, moisture, can destabilize the yeast.

Producers of dry mix packages for bakery mixes experience the limitations of yeast in their dry mix packages. There is sufficient moisture in the flour and the other components in the dry mix package to eventually destabilize the yeast included in the package. Due to the presence of moisture, the yeast begins to activate and produce carbon dioxide while still in the package mix. As a consequence, when the package mix is ready to be used by the consumer, the level of activity of the yeast is insufficient to produce carbon dioxide required to fully expand the cell structure of the dough. Thus, since the dough does not adequately rise, the resulting baked product is organoleptically inferior to the consumer.

One approach to solve this problem is to have the yeast added directly by the consumer. However, this can lead to a number of inconsistencies, and erratic performance due to consumer mishandling.

Another approach is to package the yeast separately in smaller sachets. Therefore, the yeast is separated from the remaining components of the dry mix package. Nevertheless, this is an expensive alternative due to the high packaging costs for small amounts of yeast per sachet. Furthermore, the cost of ensuring a sachet is deposited into each dry mix package substantially adds to the cost of the package mix.

An alternative method to increase the stability of the dry mix package is to dry all the components of the package, including the flour. However, this approach is not effective since the components of the package will eventually reabsorb moisture, during storage, to a level that is damaging to the yeast.

U.S. Pat. No. 4,719,114 to Percel discloses a process for preserving active dry yeast. The yeast is preserved by applying a coating containing polyethylene glycol having a molecular weight in the range of about 3350 to about 8000. Percel teaches that a benefit of using higher molecular weight polymers (i.e., 3350 to 8000) is abrasion resistance.

PCT Publication No. W095/34292 to Santus describes a micro-organism encapsulated with polyethylene glycol. The encapsulates are used in foodstuffs, such as milk and fruit juices. The coating is enteric, thus resulting in the release of micro-organisms due to an increase in pH.

It is thus an object of the present invention to provide a solvent soluble encapsulated yeast having a polymer coating with a relatively low molecular weight (i.e., less than 3050) which offers abrasion resistance, stability in storage, and an improved manufacturing process as a result of lower viscosity and lower solidification temperature of the encapsulating material, for manufacturing encapsulated yeast composites for use in food compositions and food products.

SUMMARY OF THE INVENTION

The present invention includes an encapsulated yeast composite and compositions thereof, especially food compositions and products therefrom. The present invention also includes a method for preparing food compositions and products using the unique composite.

The encapsulated yeast composite includes a core which contains yeast and a coating which contains a soluble component. The soluble coating dissolves upon contact with a solvent. In a preferred embodiment, the solvent is an aqueous solvent, such as water.

The soluble coating includes polyethylene glycol having a molecular weight not greater than 3050. Preferably, the molecular weight of the polyethylene glycol is from about 1500 to about 3000, e.g., about 2000 in one embodiment.

The yeast useful in the present invention is any dry yeast, including *Saccharomyces cerevisiae*. In a preferred embodiment, the yeast is INSTANT yeast. The minimum amount of yeast present in the composite is about 5% by weight of the composite, preferably about 30%, and more preferably about 50% by weight of the composite. The maximum amount of yeast present in the composite is about 95% by weight of the composite, preferably about 90%, and more preferably about 85% of the composite.

The food composition contains the encapsulated yeast composite. In a preferred embodiment, the food composition is a dry mix package.

The food product includes the composite which is combined with other food ingredients. The combination is subjected to a solvent which releases the yeast. In a preferred embodiment, the addition of a solvent to the combination results in a dough. The dough can be proofed and baked to obtain a food product. Preferably, the food product is a bakery product, and more preferably, a bread product.

As a result of the present invention, yeast is provided which can tolerate storage conditions (e.g., moisture) encountered by food compositions, such as dry mix packages. A low molecular weight polyethylene glycol coating protects the yeast from the environment and provides greater solubility in a solvent without detracting from the abrasion resistance of the coating. A greater solubility for polyethylene glycol allows for quicker release of the yeast, thus resulting in greater carbon dioxide production and improved leavening capacity. Moreover, a lower molecular weight polyethylene glycol exhibits a lower viscosity, enabling the coating to be more rapidly applied at a lower temperature. In addition, the lower weight polyethylene glycol also has a lower solidification temperature. The lower temperatures used during the encapsulation process are less detrimental to the viability of the yeast.

For a better understanding of the present invention, together with other and further advantages, reference is made to the following detailed description, and its scope will be pointed out in the claims.

DETAILED DESCRIPTION OF THE INVENTION

An encapsulated yeast according to the present invention is a composite which includes a core containing yeast and a coating which encapsulates the core. The minimum amount of yeast present in the composite is about 5% by weight of the composite, preferably about 30%, and more preferably about 50% by weight of the composite. The maximum amount of yeast present in the composite is about 95% by weight of the composite, preferably about 90%, and more preferably about 85% of the composite.

The coating for an encapsulated yeast is preferably a soluble coating. In a preferred embodiment, the coating is water soluble. The coating can also contain additives.

Typically, the additives can be used to enhance stability of the coating and dispersibility.

The coating completely surrounds the yeast such that the yeast is protected from the surrounding environment until it is released at the appropriate time. The appropriate time useful in the present invention can be determined by controlling the time a solvent is added to the composite.

Solvents useful in the present invention include any solvents which dissolve the coating. Preferably, the solvent is a polar solvent, especially aqueous solvents. An aqueous solvent is a liquid which contains essentially water, e.g., milk. Preferably, the aqueous solvent is water.

The soluble coating can be any coating which dissolves when in contact with a solvent, e.g., an aqueous solvent. Polymers can be part of the soluble coating, such as, for example, polyethylene glycol.

Polyethylene glycol is a polymer which is formed by condensation of ethylene glycol. The general formula for polyethylene glycol is $HOCH_2(CH_2OCH_2)_nCH_2OH$ or $H(OCH_2CH_2)_nOH$. The polyethylene glycol useful in the present invention is any low molecular weight polymer of ethylene glycol where n is any number such that the molecular weight of the polyethylene glycol is less than 3050. In a preferred embodiment, the molecular weight of the polyethylene glycol is from about 1500 to about 3000, and, in an especially preferred embodiment is about 2000.

Yeast useful in the present invention is any dry yeast which generates carbon dioxide which is beneficial for proofing of dough. For example, the yeast can be *Saccharomyces cerevisiae*. In a preferred embodiment, the yeast is INSTANT yeast.

INSTANT yeast as used herein is a highly active yeast which does not need to be prefermented (i.e., reconstituted with water and sugar) before use. INSTANT yeast activates rapidly in warm water. Some examples of INSTANT yeast include Rapid Rise Yeast and Bread Machine Yeast.

The composites of the present invention can be stored at room, refrigeration, or frozen temperatures for up to a year or more. Typically, room temperature is from about 60° F. to about 80° F. Refrigeration temperature is usually from about 34° F. to about 46° F. and frozen temperatures are typically less than about 20° F.

Food compositions contemplated as part of the present invention are those food compositions which beneficially include an encapsulated yeast composite having a soluble coating of polyethylene glycol. The compositions can, for example, include flour, dry eggs, sugar and salt. The amounts and proportions of each ingredient useful for the composition of the present invention is known to those skilled in the art. The composition can, for example, be a dry mix package. The dry mix package contains the necessary particulate components which is convertible to a dough by an addition of a solvent.

As stated above, the dry mix package which is purchased by the consumer can be reconstituted with a solvent to form a dough. The dry mix package can be stored at room, refrigeration, or frozen temperatures. Preferably, the dry mix package is stored at room temperature. The dry mix packages can be stored for an extended period of time. Typically, the storage period can be up to one year or more.

A food product can be prepared by combining an encapsulated yeast composite of the present invention with other ingredients. These components can be combined by any method known in the art. The method can, for example, include mechanical means, such as a mixer, or manual means, such as by hand.

The other food ingredients can, for example, include flour, dry eggs, sugar and salt. The amounts and proportions of encapsulated yeast composites and the other food ingredients are known to those skilled in the art. The combination formed can be a dry mix package, which can be reconstituted with a solvent to form a dough. Reconstitution with a solvent also results in release of the yeast.

When the encapsulated yeast composite is included in a dry mix package to form a dough, proofing is usually one of the steps for preparing a food product. Proofing is a process where yeast converts sugar into carbon dioxide, thereby allowing the dough to rise. As stated above, proofing is initiated by subjecting the combination (e.g., dry mix package) to a solvent to form a dough.

The dough can be proofed at a temperature from about 85° F. to about 110° F. Preferably, the dough is proofed from about 90° F. to about 105° F. After proofing, the dough is baked at a temperature known to those skilled in the art, to provide a food product (e.g., bread).

The food product can be any food product which beneficially include an encapsulated yeast composite. Some examples of a food product include, for example, a pizza crust or a bakery product. The bakery product can be, for example, a roll, bun, biscuit, or bread. Preferably, the bakery product is a bread product.

EXAMPLES

Example 1

Encapsulation of Yeast With Low Molecular Weight Polymer

Yeast, such as INSTANT yeast, is coated by spraying the molten low molecular weight polyethylene glycol coating onto the yeast using an encapsulation process. An example of an encapsulation process is a fluidized bed spray applicator as shown in U.S. Pat. No. 3,913,847 and is hereby incorporated by reference in its entirety. The method of coating is not limited, however, to the process shown in U.S. Pat. No. 3,913,847. One of ordinary skill in the art will appreciate that the present invention may also be practiced utilizing other encapsulation processes, such as spray chilling and spinning disk.

Using the fluidized bed coating method, the yeast is introduced into an encapsulation vessel (e.g., fluidized bed). The air flow passing through the fluidized bed is adjusted so that the yeast particles become slightly levitated. The yeast inside the fluidized bed are sprayed with molten polyethylene glycol of low molecular weight (e.g., less than 3,050). The lower viscosity of the low molecular weight polyethylene glycol (see Table 1) enables the coating to be more rapidly applied, effectively reducing the process time for encapsulation. The shorter application period decreases the amount of time in which the yeast is exposed to the process temperature. Furthermore, the low molecular weight polyethylene glycol solidifies at a lower temperature. This lower temperature is beneficial to the yeast encapsulation process by allowing for application of the coating at a temperature which is less detrimental to the viability of the yeast.

The low molecular weight polyethylene glycol coating protects the yeast by resisting abrasion, and functions as a barrier to oxygen. The encapsulated yeast composites result in extended storage of the yeast.

Example 2

Comparison of Composites With Different Molecular Weight Polyethylene Glycol

Several runs are made comparing the characteristics of yeast having polymer coatings (polyethylene glycol) of various molecular weights. In particular, yeast is coated by encapsulation with polymers of various molecular weights by the method as described above. Once the yeast coated with the various molecular weight polymers are prepared, tests are conducted to determine the resistance of degradation due to abrasion and the various solubilities, viscosities, and solidification temperatures of each of the polymer coatings.

TABLE 1

Solubility and Viscosity of Composites With Various Polymers of Polyethylene Glycol.

| Molar Mass (g/mole) | Solubility in Water at 20° C. (% PEG) | Viscosity at 20° C. (mPas · s) | Solidification Temperature in 50% aqueous solution (° C) |
|---|---|---|---|
| 5600–6600 | 54 | 220–262 | 55–60 |
| 3050–3700 | 56 | 85–100 | 53–57 |
| 1800–2200 | 58 | 50–56 | 48–52 |

The composites prepared with low molecular weight polymers exhibit rather good and unexpected resistance to abrasion. The abrasion resistance (e.g., rotating drum ball test) of the composites prepared with low molecular weight polymers is surprisingly similar to that of the composites prepared with high molecular weight polymers (e.g., greater than 3050). However, the solubilities of the composites prepared with low molecular weight polymers (polyethylene glycol) having a molecular weight not greater than 3,050 show an increase in solubility in an aqueous environment (see Table 1). Furthermore, the low molecular weight polyethylene glycol exhibits lower viscosity and lower solidification temperatures. The lower viscosity and lower solidification temperatures of the low molecular weight polyethylene glycol aids in the encapsulation of yeast, allowing the encapsulation process to occur at temperatures which are less harmful to the viability of the yeast, and for shorter periods of time.

Thus, as a result of the present invention, composites can be prepared (in compositions and products therefrom) which continue to protect yeast in the normal environments and under normally mechanically stressed conditions such as abrasion resulting from packaging and shipping.

Thus, while there have been described what are presently believed to be the preferred embodiments of the invention, changes and modifications can be made to the invention and other and further embodiments will be known to those skilled in the art, which fall within the spirit of the invention and it is intended to include all such other changes and modifications and embodiments as come within the scope of the claims as set forth hereinbelow.

What is claimed is:

1. An encapsulated yeast composite comprising:
    (a) a core which comprises yeast; and
    (b) a coating which comprises a soluble coating comprising polyethylene glycol having a molecular weight less than 3050.
2. A composite according to claim 1, wherein the molecular weight of polyethylene glycol is from about 1500 to about 3000.
3. A composite according to claim 2, wherein the molecular weight of polyethylene glycol is about 2000.
4. A composite according to claim 1, wherein said coating dissolves upon contact with a solvent.
5. A composite according to claim 4, wherein said solvent is an aqueous solvent.
6. A composite according to claim 1, wherein said yeast is *Saccharomyces cerevisiae*.
7. A composite according to claim 6, wherein said yeast is INSTANT yeast.
8. A composite according to claim 1, wherein said yeast is present in an amount from about 5% to 95% by weight of the composite.
9. A composite according to claim 8, wherein the yeast is present in an amount not less than about 30% by weight of the composite.
10. A composite according to claim 9, wherein the yeast is present in an amount not less than about 50% by weight of the composite.
11. A composite according to claim 8, wherein the yeast is present in an amount not greater than about 90% by weight of the composite.
12. A composite according to claim 11, wherein the yeast is present in an amount not greater than 85% by weight of the composite.
13. A food composition comprising an encapsulated yeast composite which comprises:
    (a) a core comprising yeast; and
    (b) a coating which comprises a soluble coating comprising polyethylene glycol having a molecular weight less than 3050.
14. A composition according to claim 13, wherein the molecular weight of polyethylene glycol is from about 1500 to about 3000.
15. A composition according to claim 14, wherein the molecular weight of polyethylene glycol is about 2000.
16. A composition according to claim 13, wherein said coating dissolves upon contact with an aqueous solvent.
17. A composition according to claim 16, wherein said aqueous solvent is water.
18. A composition according to claim 13, wherein said yeast is *Saccharomyces cerevisiae*.
19. A composition according to claim 18, wherein said yeast is INSTANT yeast.
20. A composition according to claim 13, wherein said composition is a dry mix package.
21. A method for preparing a food product comprising:
    (a) combining an encapsulated yeast composite, which comprises a core comprising yeast and a coating which comprises a soluble coating comprising polyethylene glycol having a molecular weight less than 3050, with other food ingredients; and
    (b) subjecting said combination from step (a) to an aqueous solvent which releases said yeast.
22. A method according to claim 21, wherein the molecular weight of polyethylene glycol is from about 1500 to 3000.
23. A method according to claim 22, wherein the molecular weight of polyethylene glycol is about 2000.
24. A method according to claim 21, wherein said aqueous solvent is water.
25. A method according to claim 21, wherein said yeast is *Saccharomyces cerevisiae*.
26. A method according to claim 25, wherein said yeast is INSTANT yeast.
27. A method according to claim 21, wherein said composition is a dry mix package.
28. A method according to claim 27, wherein said dry mix package is stored at room temperature.
29. A method according to claim 21, wherein said composition from step (b) is dough.
30. A method according to claim 29, further comprising proofing and baking said dough.

31. A method according to claim 21, wherein said food product is a bakery product.

32. A method according to claim 31, wherein said bakery product is a bread product.

33. A food product prepared according to a method comprising:
   (a) combining an encapsulated yeast composite, which comprises a core comprising yeast and a coating which comprises a soluble coating comprising polyethylene glycol having a molecular weight less than 3050, with other food ingredients; and
   (b) subjecting said combination from step (a) to an aqueous solvent which releases said yeast.

34. A food product according to claim 33, wherein the molecular weight of polyethylene glycol is from about 1500 to about 3000.

35. A food product according to claim 34, wherein the molecular weight of polyethylene glycol is about 2000.

36. A food product according to claim 33, wherein said coating dissolves upon contact with an aqueous solvent.

37. A food product according to claim 36 wherein said aqueous solvent is water.

38. A food product according to claim 33, wherein said yeast is *Saccharomyces cerevisiae*.

39. A food product according to claim 38, wherein said yeast is INSTANT yeast.

40. A food product according to claim 33, wherein said combination is stored at room temperature.

41. A food product according to claim 33, wherein said combination is a dry mix package.

42. A food product according to claim 33, wherein said composition from step (b) is a dough.

43. A food product according to claim 42, wherein said dough is proofed and then baked.

44. A food product according to claim 33, wherein said food product is pizza crust.

45. A food product according to claim 33, wherein said food product is a bakery product.

46. A food product according to claim 45, wherein said bakery product is a bread product.

* * * * *